(12) United States Patent
Abuto

(10) Patent No.: US 6,765,125 B2  
(45) Date of Patent: *Jul. 20, 2004

(54) DISTRIBUTION—RETENTION MATERIAL FOR PERSONAL CARE PRODUCTS

(75) Inventor: Frank Paul Abuto, Duluth, GA (US)

(73) Assignee: Kimberly-Clark Worldwide, Inc., Neenah, WI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/249,127

(22) Filed: Feb. 12, 1999

(65) Prior Publication Data

US 2001/0053904 A1 Dec. 20, 2001

(51) Int. Cl.⁷ .................. A61F 13/15; A61F 13/20
(52) U.S. Cl. ............... 604/378; 604/368; 604/385.01
(58) Field of Search ...................... 604/368, 385.01, 604/378

(56) References Cited

U.S. PATENT DOCUMENTS

| | | | |
|---|---|---|---|
| 2,024,976 A | 12/1935 | Mathey et al. | 128/290 |
| 3,338,992 A | 8/1967 | Kinney | 264/24 |
| 3,341,394 A | 9/1967 | Kinney | 161/72 |
| 3,502,763 A | 3/1970 | Hartmann | 264/210 |
| 3,542,615 A | 11/1970 | Dobo et al. | 156/181 |
| 3,692,618 A | 9/1972 | Dorschner et al. | 161/72 |
| 3,802,817 A | 4/1974 | Matsuki et al. | 425/66 |
| 3,849,241 A | 11/1974 | Butin et al. | 161/169 |
| 4,005,957 A | 2/1977 | Savich | 425/80 |
| 4,100,324 A | 7/1978 | Anderson et al. | 428/288 |
| 4,327,728 A * | 5/1982 | Elias | 604/368 |
| 4,340,563 A | 7/1982 | Appel et al. | 264/518 |

(List continued on next page.)

FOREIGN PATENT DOCUMENTS

| | | | | |
|---|---|---|---|---|
| DE | 35 08 344 | 9/1986 | | A61F/13/00 |
| EP | 0 217 666 | 4/1987 | | A41B/13/02 |

(List continued on next page.)

OTHER PUBLICATIONS

*Polymer Blends and Composites* by John A. Manson and Leslie H. Sperling, copyright 1976 by Plenum Press, a division of Plenum Publishing Corporation of New York, IBSN 0–306–30831–2, at pp. 273 through 277.

*Primary Examiner*—John J. Calvert  
*Assistant Examiner*—Michele Kidwell  
(74) *Attorney, Agent, or Firm*—Steven D. Flack

(57) ABSTRACT

There is provided a distribution/retention layer for personal care products which is a nonwoven fabric having retention materials and distribution materials in a side-by-side configuration as rows, stripes, channels, etc. These rows may be continuous or discontinuous and may be straight, wavy, or in other patterns. This construction allows liquid to wick along the distribution rows and to be absorbed by the retention material along a broad front on either side. Such a construction more fully utilizes the absorbent core, producing cost and weight savings. This construction also provides greater comfort to a wearer.

There is further provided personal care products having the nonwoven web as a component.

11 Claims, 2 Drawing Sheets

U.S. PATENT DOCUMENTS

| | | | | |
|---|---|---|---|---|
| 4,360,021 A | | 11/1982 | Stima | 128/287 |
| 4,381,783 A | | 5/1983 | Elias | 604/368 |
| 4,388,056 A | | 6/1983 | Lee et al. | 425/83.1 |
| 4,578,070 A | | 3/1986 | Holtman | 604/378 |
| 4,592,708 A | | 6/1986 | Feist et al. | 425/80.1 |
| 4,598,441 A | | 7/1986 | Stemmler | 19/145 |
| 4,636,209 A | | 1/1987 | Lassen | 604/378 |
| 4,674,996 A | | 6/1987 | Anno et al. | 474/110 |
| 4,761,258 A | | 8/1988 | Enloe | 264/518 |
| 4,764,325 A | | 8/1988 | Angstadt | 264/113 |
| 4,818,464 A | | 4/1989 | Lau | 264/510 |
| RE32,957 E | | 6/1989 | Elias | 604/368 |
| 4,904,440 A | | 2/1990 | Angstadt | 264/517 |
| 4,908,175 A | | 3/1990 | Angstadt | 264/113 |
| 5,004,579 A | | 4/1991 | Wislinski et al. | 264/517 |
| 5,057,368 A | | 10/1991 | Largman et al. | 428/397 |
| 5,069,970 A | | 12/1991 | Largman et al. | 428/373 |
| 5,108,820 A | | 4/1992 | Kaneko et al. | 428/198 |
| 5,108,827 A | | 4/1992 | Gessner | 428/219 |
| 5,118,376 A | * | 6/1992 | Pigneul et al. | 156/219 |
| 5,200,248 A | | 4/1993 | Thompson et al. | 428/131 |
| 5,242,644 A | | 9/1993 | Thompson et al. | 264/177.15 |
| 5,268,229 A | | 12/1993 | Phillips et al. | 428/400 |
| 5,277,976 A | | 1/1994 | Hogle et al. | 428/397 |
| 5,336,552 A | | 8/1994 | Strack et al. | 428/224 |
| 5,382,400 A | | 1/1995 | Pike et al. | 264/168 |
| 5,411,497 A | | 5/1995 | Tanzer et al. | 604/368 |
| 5,425,725 A | | 6/1995 | Tanzer et al. | 604/368 |
| 5,433,715 A | | 7/1995 | Tanzer et al. | 604/368 |
| 5,466,410 A | | 11/1995 | Hills | 264/172.11 |
| H1511 H | | 12/1995 | Chappell et al. | 604/383 |
| 5,575,785 A | | 11/1996 | Gryskiewicz et al. | 604/385.2 |
| 5,593,399 A | | 1/1997 | Tanzer et al. | 604/368 |
| 5,601,542 A | | 2/1997 | Melius et al. | 604/368 |
| 5,611,981 A | | 3/1997 | Phillips et al. | 264/130 |
| 5,643,238 A | | 7/1997 | Baker | 604/368 |
| 5,649,914 A | | 7/1997 | Glaug et al. | 604/361 |
| 5,681,298 A | | 10/1997 | Brunner et al. | 604/361 |
| 5,702,376 A | | 12/1997 | Glaug et al. | 604/361 |
| 5,723,159 A | | 3/1998 | Phillips et al. | 425/461 |
| 5,785,697 A | * | 7/1998 | Trombetta et al. | 604/378 |
| 5,814,035 A | | 9/1998 | Gryskiewicz et al. | 604/385.1 |
| 5,856,366 A | | 1/1999 | Shiveley et al. | |
| 5,863,288 A | | 1/1999 | Baker | |
| 5,866,173 A | | 2/1999 | Reiter et al. | |
| 6,080,909 A | * | 6/2000 | Osterdahl et al. | 604/368 |

FOREIGN PATENT DOCUMENTS

| | | | | |
|---|---|---|---|---|
| EP | 0 391 814 | | 10/1990 | D01D/5/253 |
| EP | 0 151 033 | | 7/1995 | A61F/13/15 |
| EP | 0 804 915 | | 11/1997 | A61F/13/15 |
| EP | 0 804 916 | | 11/1997 | A61F/13/15 |
| EP | 0 804 917 | | 11/1997 | A61F/13/15 |
| EP | 0 815 817 | | 1/1998 | A61F/13/15 |
| GB | 2 191 793 | | 12/1987 | D01G/23/08 |
| WO | 94/06385 | | 3/1994 | A61F/13/15 |
| WO | 94/23761 | | 10/1994 | |
| WO | 95/10996 | | 4/1995 | |
| WO | 95/11651 | | 5/1995 | A61F/13/15 |
| WO | 95/13777 | | 5/1995 | A61F/13/46 |
| WO | 95/13778 | | 5/1995 | A61F/13/46 |
| WO | 95/13779 | | 5/1995 | A61F/13/46 |
| WO | 95/16422 | | 6/1995 | A61F/13/15 |
| WO | 95/17870 | | 7/1995 | |
| WO | 95/27457 | | 10/1995 | A61F/13/15 |
| WO | 95/31167 | | 11/1995 | A61F/13/15 |
| WO | 96/40030 | | 12/1996 | A61F/13/15 |
| WO | 98/07909 | | 2/1998 | D01D/5/253 |
| WO | 98/07910 | | 2/1998 | D01D/5/253 |
| WO | 98/51250 | | 11/1998 | |
| WO | 99/47094 | | 9/1999 | |
| WO | 99/63922 | | 12/1999 | |
| WO | 00/37001 | | 6/2000 | |
| WO | 00/38749 | | 7/2000 | |

* cited by examiner

DISTRIBUTION— RETENTION MATERIAL FOR PERSONAL CARE PRODUCTS

FIELD OF THE INVENTION

The present invention relates to a structure in an article for personal care like diapers, training pants, absorbent underpants, adult incontinence products, bandages and feminine hygiene products, which can accept liquid, distribute it and retain it.

BACKGROUND OF THE INVENTION

Personal care articles include such items as diapers, training pants, feminine hygiene products such as sanitary napkins, panty-liners and tampons, incontinence garments and devices, bandages and the like. The most basic design of all such articles typically includes a bodyside liner, an outercover and an absorbent core disposed between the bodyside liner and the outercover.

Personal care products must accept fluids quickly and hold them to reduce the possibility of leakage outside the product. The product must be flexible and have a pleasing feel on the skin, and even after liquid insult, must not become tight or bind the user. Unfortunately, while previous products have met many of these criteria to varying degrees, a number have not.

The use of superabsorbents in personal care products has become common. The expansion of such superabsorbents upon exposure to bodily fluids, however, has been known to block further acceptance of liquid, a phenomenon known as "wet collapse" or "gel blocking". Wet collapse eliminates void space for fluid to enter and can render the absorbent ineffective, preventing the absorption of additional liquid despite the availability of unused or unsaturated superabsorbent within. Superabsorbent expansion can also reduce or eliminate fluid distribution via wicking.

In order to achieve greater integrity and resilience, a variety of product construction methods and materials have been tried. These have included gluing absorbent core layers together, embossing the absorbent core layers, adding reinforcing materials to the absorbent core and adding a resilient element of the absorbent core to hold the structure open and retain void space.

Each of these approaches has resulted in some compromise in the absorbent and/or comfort features of the product. Glues and adhesives, for example, tend to be hydrophobic and so interfere with the absorption of bodily fluids into the product. Embossing increases the integrity of the absorbent core by increasing its density but in so doing reduces the void volume needed for fluid intake and retention. The addition of reinforcing and resilient material likewise has proven unsatisfactory.

There remains a need, therefore, for a material that will maintain its ability to accept fluid flow as well as absorb liquid without significant detrimental wet collapse.

It is an object of this invention, therefore, to provide an absorbent structure that can accept fluids while maintaining void volume. It is another object of this invention to provide a structure that will "wick" or distribute liquid so that a greater amount of superabsorbent is utilized.

SUMMARY OF THE INVENTION

The objects of the invention are achieved by a distribution/retention layer for personal care products which is a nonwoven fabric having retention materials and distribution materials in a side-by-side configuration as rows, stripes, channels, etc. These rows may be continuous or discontinuous and may be straight, wavy, or in other patterns.

There is further provided personal care products having the absorbent structure as a component.

DEFINITIONS

Figure 1:
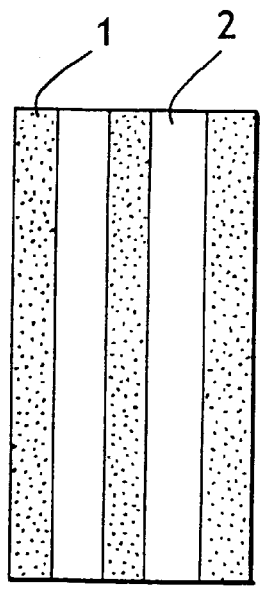
FIG. 1 is a diagram of a distribution/retention layer wherein the (darker) retention rows are about 13 mm wide deposited in continuous straight lines.

"Disposable" includes being disposed of after use and not intended to be washed and reused.

"Hydrophilic" describes fibers or the surfaces of fibers that are wetted by the aqueous liquids in contact with the fibers. The degree of wetting of the materials can, in turn, be described in terms of the contact angles and the surface tensions of the liquids and materials involved. Equipment and techniques suitable for measuring the wettability of particular fiber materials can be provided by a Cahn SFA-222 Surface Force Analyzer System, or a substantially equivalent system. When measured with this system, fibers having contact angles less than 90° are designated "wettable" or hydrophilic, while fibers having contact angles equal to or greater than to 90° are designated "nonwettable" or hydrophobic.

"Layer" when used in the singular can have the dual meaning of a single element or a plurality of elements.

"Liquid" means a non-particulate substance and/or material that flows and can assume the interior shape of a container into which it is poured or placed.

"Liquid communication" means that liquid is able to travel from one layer to another layer, or one location to another within a layer.

"Longitudinal" means having the longitudinal axis in the plane of the article and is generally parallel to a vertical plane that bisects a standing wearer into left and right body halves when the article is worn. The "transverse" axis lies in the plane of the article generally perpendicular to the longitudinal axis, i.e., so that a vertical plane bisects a standing wearer into front and back body halves when the article is worn.

"Conjugate fibers" refers to fibers that have been formed from at least two polymers extruded from separate extruders but spun together to form one fiber. Conjugate fibers are also sometimes referred to as multicomponent or bicomponent fibers. The polymers are usually different from each other though conjugate fibers may be monocomponent fibers. The polymers are arranged in substantially constantly positioned distinct zones across the cross-section of the conjugate fibers and extend continuously along the length of the conjugate fibers. The configuration of such a conjugate fiber may be, for example, a sheath/core arrangement wherein one polymer is surrounded by another or may be a side by side arrangement, a pie arrangement or an "islands-in-the-sea" arrangement. Conjugate fibers are taught in U.S. Pat. No. 5,108,820 to Kaneko et al., U.S. Pat. No. 5,336,552 to Strack et al., and U.S. Pat. No. 5,382,400 to Pike et al. For two component fibers, the polymers may be present in ratios of 75/25, 50/50, 25/75 or any other desired ratios. The fibers may also have shapes such as those described in U.S. Pat. Nos. 5,277,976 to Hogle et al., and U.S. Pat. Nos. 5,069,970 and 5,057,368 to Largman et al., hereby incorporated by reference in their entirety, which describe fibers with unconventional shapes.

"Biconstituent fibers" refers to fibers that have been formed from at least two polymers extruded from the same extruder as a blend. Biconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Biconstituent fibers are sometimes also referred to as multiconstituent fibers. Fibers of this general type are discussed in, for example, U.S. Pat. No. 5,108,827 to Gessner. Bicomponent and biconstituent fibers are also discussed in the textbook *Polymer Blends and Composites* by John A. Manson and Leslie H. Sperling, copyright 1976 by Plenum Press, a division of Plenum Publishing Corporation of New York, IBSN 0-306-30831-2, at pages 273 through 277.

As used herein, the term "machine direction" or MD means the length of a fabric in the direction in which it is produced. The term "cross machine direction" or CD means the width of fabric, i.e. a direction generally perpendicular to the MD.

As used herein the term "spunbonded fibers" refers to small diameter fibers which are formed by extruding molten thermoplastic material as filaments from a plurality of fine, usually circular capillaries of a spinneret with the diameter of the extruded filaments then being rapidly reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, and U.S. Pat. No. 3,542,615 to Dobo et al. Spunbond fibers are generally not tacky when they are deposited onto a collecting surface. Spunbond fibers are generally continuous and have average diameters (from a sample of at least 10) larger than 7 microns, more particularly, between about 10 and 35 microns. The fibers may also have shapes such as those described in U.S. Pat. No. 5,277,976 to Hogle et al., U.S. Pat. Nos. 5,466,410 to Hills and U.S. Pat. Nos. 5,069,970 and 5,057,368 to Largman et al., which describe fibers with unconventional shapes.

As used herein the term "meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly dispersed meltblown fibers. Such a process is disclosed, for example, in U.S. Pat. No. 3,849,241 to Butin et al. Meltblown fibers are microfibers that may be continuous or discontinuous, are generally smaller than 10 microns in average diameter, and are generally tacky when deposited onto a collecting surface.

"Capillary Surface Materials" or CSMs are oriented surface fibers or groups of such fibers which can spontaneously transport certain fluids. Fibers of this general type are discussed in, for example, PCT/US97/14861, PCT/US97/14607, European Patent Application 90420164.7, and U.S. Pat. Nos. 5,200,248, 5,242,644, 5,268,229, 5,611,981 and 5,723,159.

"Airlaying" is a well-known process by which a fibrous nonwoven layer can be formed. In the airlaying process, bundles of small fibers having typical lengths ranging from about 3 to about 52 millimeters are separated and entrained in an air supply and then deposited onto a forming screen, usually with the assistance of a vacuum supply. The randomly deposited fibers then are bonded to one another using, for example, hot air or a spray adhesive. Airlaying is discussed in, for example, U.S. Pat. Nos. 4,005,957, 4,388,056, 4,592,708, 4,598,441, 4,674,996, 4,761,258, 4,764,325, 4,904,440, 4,908,175, and 5,004,579, German Patent DE3508344 A1, European Patent Application 85300626.0 and British Patent Application 2,191,793.

As used herein, the term "coform" means a process in which at least one meltblown diehead is arranged near a chute through which other materials are added to the web while it is forming. Such other materials may be pulp, superabsorbent or other particles, natural polymers (for example, rayon or cotton fibers) and/or synthetic polymers (for example, polypropylene or polyester) fibers, for example, where the fibers may be of staple length. Coform processes are shown in commonly assigned U.S. Pat. No. 4,818,464 to Lau and U.S. Pat. No. 4,100,324 to Anderson et al. Webs produced by the coform process are generally referred to as coform materials.

"Bonded carded web" refers to webs that are made from staple fibers that are sent through a combing or carding unit, which breaks apart and aligns the staple fibers in the machine direction to form a generally machine direction-oriented fibrous nonwoven web. The web is bonded by one or more of several known bonding methods.

Bonding of nonwoven webs may be achieved by a number of methods; powder bonding, wherein a powdered adhesive is distributed through the web and then activated, usually by heating the web and adhesive with hot air; pattern bonding, wherein heated calender rolls or ultrasonic bonding equipment are used to bond the fibers together, usually in a localized bond pattern, though the web can be bonded across its entire surface if so desired; through-air bonding, wherein air which is sufficiently hot to soften at least one component of the web is directed through the web; chemical bonding using, for example, latex adhesives that are deposited onto the web by, for example, spraying; and consolidation by mechanical methods such as needling and hydroentanglement.

Figure 3:
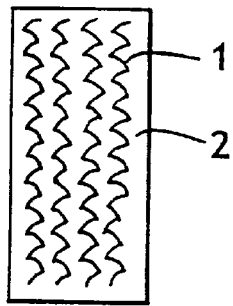
FIG. 3 is a diagram of a distribution/retention layer wherein the (darker) retention rows are deposited in continuous wavy lines.

"Perpendicularly laid" or "Z-directional fabrics" are fabrics in which the fibers are oriented in a direction perpendicular to the predominant plane (X-Y) of the fabric. This predominant plane is also generally the MD-CD plane. FIG. 3 indicates the direction of the three axes.

"Personal care product" means diapers, training pants, absorbent underpants, adult incontinence products, swim wear, bandages and other wound dressings, and feminine hygiene products.

"Feminine hygiene products" means sanitary napkins, pads and tampons. "Target area" refers to the area or position on a personal care product where an insult is normally delivered by a wearer.

Test Methods

Material caliper (thickness): The caliper of a material is a measure of thickness and is measured at 0.05 psi with a Starret-type bulk tester, in units of millimeters.

Density: The density of the materials is calculated by dividing the weight per unit area of a sample in grams per square meter (gsm) by the bulk of the sample in millimeters (mm) at 68.9 Pascals and multiplying the result by 0.001 to convert the value to grams per cubic centimeter (g/cc). A total of three samples would be evaluated and averaged for the density values.

DETAILED DESCRIPTION OF THE INVENTION

A personal care product typically has a body side layer, optionally a fluid transfer layer, a fluid retention layer and a garment side layer acting together as an absorbent system. It may also have a distribution layer or other optional layers to provide specialized functions. This absorbent system for a personal care product, comprised of layers positioned between the body side and garment side layers, must take in and distribute fluid in a controlled manner away from contact with the body.

The body side layer is sometimes referred to as a bodyside liner or topsheet. In the thickness direction of the article, the liner material is the layer against the wearer's skin and so the first layer in contact with liquid or other exudate from the wearer. The liner further serves to isolate the wearer's skin from the liquids held in an absorbent structure and should be compliant, soft feeling and non-irritating. The body side liner can be surface treated with a selected amount of surfactant, or otherwise processed to impart the desired level of wettability and hydrophilicity.

The garment side liner layer, also referred to as a backsheet or outer cover is the farthest layer from the wearer. The outer cover has traditionally been formed of a thin thermoplastic film, such as polyolefin (i.e. polyethylene) film, which is substantially impermeable to liquid. The outer cover functions to prevent body exudates contained in an absorbent structure from wetting or soiling the wearer's clothing, bedding, or other materials contacting the personal care product. The outer cover may be, for example, a polyethylene film having an initial thickness of from about 0.5 mil (0.012 millimeter) to about 5.0 mil (0.12 millimeter) and a basis weight of from about 10 to about 100 gsm, or may comprise synthetic fibers and binder in a ratio of from about 50/50 to about 0/100.

The outer cover may be embossed and/or matte finished to provide a more aesthetically pleasing appearance. Other alternative constructions for outer cover include woven or nonwoven fibrous webs or laminates formed of a woven or nonwoven fabric and thermoplastic film. The outer cover may optionally be composed of a vapor or gas permeable, microporous "breathable" material, that is permeable to vapors or gas yet substantially impermeable to liquid. Outer covers may also serve the function of a mating member for mechanical fasteners.

The absorbent system located between the body side and garment side layers must absorb liquid from the adjacent body side layer in a controlled manner such that liquid may be stored away from contact with the body. In so doing, wet collapse should be avoided to the greatest extent possible. In addition, wicking and movement of the fluid from the point of deposition, the target area, should be maximized in order to use the superabsorbent material to its maximum capability and to ready the target area for additional insults. Various designs have been proposed to achieve this result by providing separate distribution and retention layers on top of each other. In addition, previous absorbent cores have used, for example, homogeneous mixtures of superabsorbents and pulp fluff. The fluff in this mixture becomes relatively ineffective in the transportation of liquid as the superabsorbent expands to absorb the liquid, resulting in the curtailment of distribution within the mixture. The inventors have found a way to achieve the desired result in a single layer.

The inventive material has rows, zones, stripes or channels of alternating distribution and retention materials. This spaced apart construction allows liquid to wick along the distribution rows and to be absorbed by the retention material along a broad front on either side. Such a construction more fully utilizes the absorbent core, producing cost and weight savings. This construction also provides greater comfort to a wearer since, when liquid is moved away from the target area and the retention material more efficiently used, the mass of liquid in the target area is reduced. Reducing the mass of liquid in the target area results in the reduction of the amount of sagging and bulging in a personal care product such as a diaper.

The spacing apart placing of retention material in rows instead of throughout the web may also enhance the air circulation (breathability) of a personal care product since the separate fibrous distribution rows are believed to be more permeable to air than a mixed fiber/superabsorbent retention material. The exchange of air within a personal care product is believed to be a factor in skin health.

The exact dimension of the distribution and retention rows must be determined by taking into consideration the end use of the material and the characteristics of the ingredients. A desirable width of each retention and distribution row is between about 5 mm and 80 mm, more particularly between about 10 and 50 mm, and still more particularly between about 10 and 25 mm. A material destined for a diaper and designed for urine absorption probably has different design criteria (e.g., different liquid viscosity, particulate content) than a material destined for feminine hygiene applications. Likewise, there exist "fast" and "slow" superabsorbents and superabsorbents are available in many different forms such as particles, fibers, flakes and spheres. The denier, wettability, density, bonding, and inter-fiber pore size are a number of the variables which must be considered by those skilled in the art in specifying the fibers to be used in the distribution rows, for example. In addition, the basis weight of the final web, and of each layer of the web if it is a laminate, must be determined based upon the ultimate use of the web. Basis weights of various layers may vary between, for example, 10 to 900 gsm and may be different in each layer. The amount of retention material may vary along the row and between rows as well, and may be between, for example, 25 and 1500 gsm. In addition, specific distribution areas may be hydrophobic which is believed to enhance breathability of the layer.

The shape or pattern of the rows may vary from simply straight lines and may be wavy or have other shapes limited only by the imagination. The pattern may be discontinuous as well, although discontinuities in the distribution row would, obviously, end liquid distribution at the end of the row of that layer.

The webs of this invention may be made by a variety of processes including airlaying, spunbonding, meltblowing, coform and foaming processes.

The distribution row materials may be made from a variety of fibers and mixtures of fibers including synthetic fibers, natural fibers including hydroentangled pulp, mechanically and chemically softened pulp, staple fibers, slivers, meltblown and spunbond fibers and the like. Capillary Surface Materials (CSMs) may be used as the distribution material as well. The fibers in such a web may be made from the same or varying diameter fibers and may be of different shapes such as pentalobal, trilobal, elliptical, round, etc.

The retention row materials may be made from materials or substances known in the art to absorb liquid as well as any others that may be developed for that purpose. Examples include fast and slow superabsorbents, pulps, and mixtures thereof. Mixtures of superabsorbents and pulp used as retention materials may be used in ratios of between about 100/0 and 20/80 by weight, more particularly between about 65/35 and 35/65.

Binder fibers may also be included in the retention and/or distribution row in order to provide mechanical integrity to the web. Preferred fibers for inclusion are those having a relatively low melting point such as polyolefin fibers. Lower melting polymers provide the ability to bond the fabric together at fiber cross over points upon the application of heat. By "lower melting polymers" what is meant are those having a glass transition temperature less than about 175° C. In addition, fibers having as at least one component a lower melting polymer, like conjugate and biconstituent fibers, are suitable for the practice of this invention. Fibers having a lower melting polymer are generally referred to as "fusible fibers."

Synthetic fibers include those made from polyamides, polyesters, rayon, polyolefins, acrylics, superabsorbents, Lyocel regenerated cellulose and any other suitable synthetic fibers known to those skilled in the art. Synthetic fibers may also include kosmotropes for product degradation.

Natural fibers include wool, cotton, flax, hemp and wood pulp. Pulps include standard soft-wood fluffing grade such as CR-1654 from Coosa Mills of Coosa, Ala., high bulk additive formaldehyde free pulp (HBAFF) available from the Weyerhaeuser Corporation of Tacoma, Wash., and is a which is a crosslinked southern softwood pulp fiber with enhanced wet modulus, and a chemically cross-linked pulp fiber such as Weyerhaeuser NHB416. HBAFF has a chemical treatment that sets in a curl and twist, in addition to imparting added dry and wet stiffness and resilience to the fiber. Another suitable pulp is Buckeye HP2 pulp and still another is IP Supersoft from International Paper Corporation. Suitable rayon fibers are 1.5 denier Merge 18453 fibers from Courtaulds Fibers Incorporated of Axis, Ala.

Various superabsorbents in a number of forms are available. Commercially available examples include FAVORS® 870 superabsorbent spheres from the Stockhausen Company of Greensboro, N.C. 27406 which is a highly crosslinked surface superabsorbent, XL AFA 94-21-5 and XL AFA-126-15, which are 850 to 1400 micron suspensions of polymerized polyacrylate particles from The Dow Chemical Company of Midland, Mich., and SANWET® IM 1500 superabsorbent granules supplied by KoSA Inc. (formerly Trevira Inc. and formerly Hoechst-Celanese), PO Box 4, Salisbury, N.C. 28145-0004.

Binders include fiber, liquid or other binder means which may be thermally activated. Exemplary binders include conjugate fibers of polyolefins and/or polyamides, and liquid adhesives. Two such suitable binders are sheath core conjugate fibers available from KoSA Inc. under the designation T-255 and T-256, though many suitable binder fibers are known to those skilled in the art, and are made by many manufacturers such as Chisso and Fibervisions LLC of Wilmington, Del. A suitable liquid binder is Kymene® 557LX binder available from Fibervisions LLC. Binders, if present, must be present in an effective amount; generally less than 15 weight percent.

Once produced, the web must be adequately stabilized and consolidated in order to retain its shape. The inclusion of a sufficient amount of fusible fibers and subsequent thermal bonding is the preferred method for obtaining adequate stabilization. It's believed that this method allows adequate bonding in the center of a thick material as well as on the surface.

The distribution-retention web of this invention may be used as a laminate. In the case of a laminate, one or more webs may be fused together by, for example, thermal bonding and stabilization. Such other layers may be woven or knitted fabrics, other nonwovens, films, tissues, paper, foil, foam, etc., and each layer may contain a variety of fibers and particles to impart particular properties.

Figure 5:
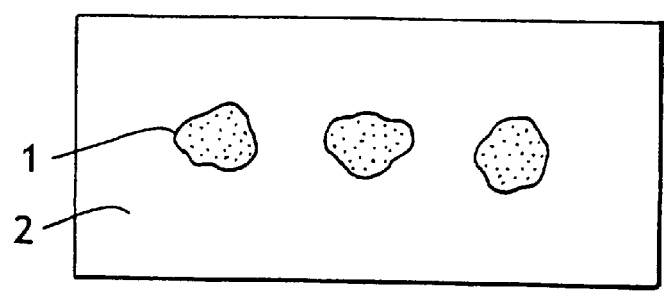
FIG. 5 is a cross sectional view of a laminate wherein the retention material is surrounded by distribution material.

One method of producing a laminate is to produce a layer of fibers by, for example, an airlaying process, deposit rows of retention material onto the layer of airlaid fibers, and then produce another layer of fibers by airlaying onto the rows of retention material. It should be noted that the use of the airlaying process to produce such a laminate usually results in the individual layers being substantially indistinguishable from each other in the laminate. A cross sectional view of such a laminate is shown in FIG. 5 wherein the retention material 1 is surrounded by distribution material 2. Another method is the production of such a laminate using the meltblowing process to produce a layer of nonwoven material (e.g. meltblown fibers) onto one or both sides of the web resulting in a sandwich-like construction.

EXAMPLES

1) Samples of the distribution-retention web of this invention were made using the coforming process. Tape was placed on the forming wire (conveyor belt) onto which fluff pulp was deposited, in a parallel, machine direction, straight line pattern such that there was a gap of about 63.5 mm between adjacent tape strips. The tape was 19 mm wide. A carrier tissue sheet was unwound onto the wire and a vacuum was applied below the wire to encourage pulp deposition. The pulp was deposited onto the forming wire between the tape strips. Just downstream of the pulp deposition, superabsorbent particles were deposited into the void spaces between the stripes of fluff pulp. By separating the superabsorbent from the rate enhancing distribution material, fluid wicking is thus not disrupted by the swelling superabsorbent.

2) A mixture of fluff pulp and about 5 weight percent binder fiber was deposited onto a forming wire using the airlaid process. On top of the fluff/binder layer was deposited superabsorbent particles. The Deposition patterns like that shown in FIGS. 1, 2, 3, and 4 were produced. The structure was then passed through a heater to activate the binder fibers and stabilize the structure. Yet another example was produced, in which additional pulp fluff and binder fiber was deposited after the superabsorbent using the airlaid process, resulting in a structure like that shown in FIG. 5.

Turning now to the Figures it can be seen that a variety of patterns are possible within the ambit of this invention. FIG.

Figure 2:
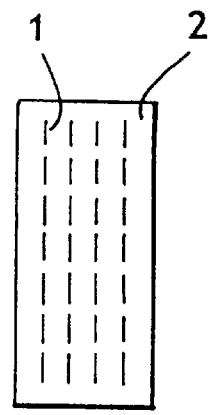
FIG. 2 is a diagram of a distribution/retention layer wherein the (darker) retention rows are deposited in discontinuous straight lines.
Figure 4:
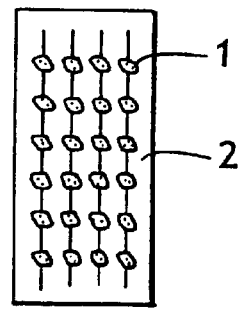
FIG. 4 is a diagram of a distribution/retention layer wherein the (darker) retention rows are deposited in continuous straight lines having additional masses of retention material deposited periodically.
Figure 6:
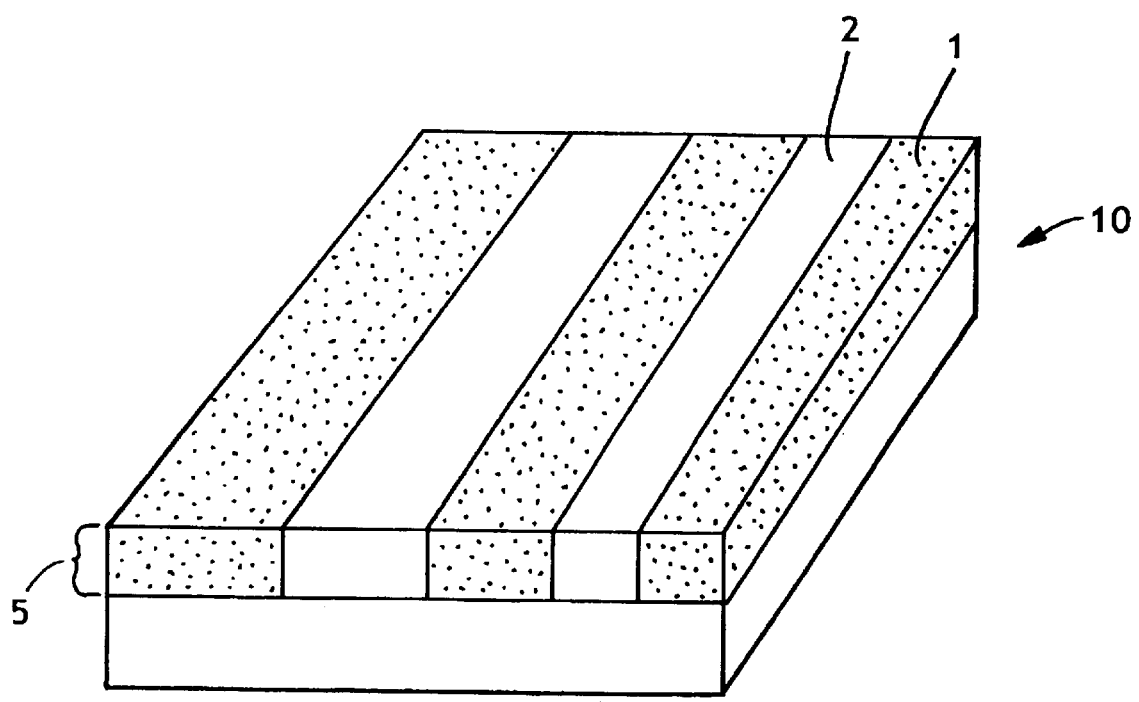
FIG. 6 is a perspective view of a laminate including a single layer of distribution/retention material wherein the darker retention rows are deposited in continuous straight channels between channels of distribution material.

1 shows a pattern of rows wherein the retention material 1 has a width of about 13 mm and the distribution material 2 has the same width and the rows have been deposited in straight lines. FIGS. 2, 3 and 4 show patterns where the retention material 1 is deposited in discontinuous lines, wavy lines, and straight lines with periodic additional masses of retention material, respectively. Similarly, FIG. 6 shows a perspective view of a laminate 10 including a single layer of distribution/retention material 5 wherein the darker retention rows 1 are deposited in continuous straight channels in a side- by -side configuration to channels of distribution material 2.

Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention as defined in the following claims. In the claims, means plus function claims are intended to cover the structures described herein as performing the recited function and not only structural equivalents but also equivalent structures. Thus although a nail and a screw may not be structural equivalents in that a nail employs a cylindrical surface to secure wooden parts together, whereas a screw employs a helical surface, in the environment of fastening wooden parts, a nail and a screw may be equivalent structures.

It should further be noted that any patents, applications or publications referred to herein are incorporated by reference in their entirety.

What is claimed is:

1. A laminate including a single combination distribution/retention layer for personal care products, said distribution/retention layer having a thickness direction, and wherein said distribution/retention layer consisting of either an airlaid nonwoven fabric or a coformed nonwoven fabric, having retention materials and distribution materials in a continuous and machine direction, and side-by-side configurations, wherein said retention and distribution materials extend completely through said distribution/retention layer in said thickness direction, and further wherein said configurations are continuous straight lines of retention and distribution channels with periodic additional masses of retention material.

2. A personal care product comprising the laminate of claim 1.

3. The personal care product of claim 2 which is a diaper.

4. The personal care product of claim 2 which is a training pant.

5. The personal care product of claim 2 which is an incontinence product.

6. The personal care product of claim 2 which is a bandage.

7. The personal care product of claim 2 which is a feminine hygiene product.

8. A process of producing a distribution/retention layer for personal care products, said distribution/retention lever having a thickness direction, said process comprising the steps of:

A) providing through processes which deposit materials through air onto a forming surface with the assistance of a vacuum, spaced apart continuous machine direction lines or stripes of distribution material with gaps therebetween, and B) then depositing within said gaps continuous machine direction lines or stripes of retention material so as to fill said gaps, wherein said retention and distribution materials extend completely through said layer in said thickness direction.

9. The process of claim 8 further comprising the step of depositing a layer of distribution material onto said retention material.

10. The process of claim 9 wherein said distribution material is a mixture of fluff pulp and binder fiber and is deposited by an airlaid process.

11. The process of claim 8 wherein said distribution material is a mixture of fluff pulp and binder fiber and is provided by an airlaid process.

\* \* \* \* \*